(12) United States Patent
Watanabe et al.

(10) Patent No.: US 9,304,085 B2
(45) Date of Patent: Apr. 5, 2016

(54) LASER SCANNING MICROSCOPE SYSTEM AND METHOD OF SETTING LASER-LIGHT INTENSITY VALUE

(71) Applicant: Sony Corporation, Tokyo (JP)

(72) Inventors: Shinji Watanabe, Tokyo (JP); Kazuki Aisaka, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/516,798

(22) Filed: Oct. 17, 2014

(65) Prior Publication Data

US 2015/0115176 A1   Apr. 30, 2015

(30) Foreign Application Priority Data

Oct. 24, 2013   (JP) .................................. 2013-221363

(51) Int. Cl.
    *G01N 21/64* (2006.01)
(52) U.S. Cl.
    CPC ........ *G01N 21/6458* (2013.01); *G01N 21/6428* (2013.01)
(58) Field of Classification Search
    CPC .............. G01N 21/64; G01N 21/6458; G01N 21/6486; G01N 21/645
    See application file for complete search history.

(56) References Cited

U.S. PATENT DOCUMENTS

2005/0179892 A1\* 8/2005 Gerstner et al. .............. 356/318

FOREIGN PATENT DOCUMENTS

JP   2012/128354 A   7/2012
JP   2012-212133 A   11/2012

\* cited by examiner

*Primary Examiner* — David Porta
*Assistant Examiner* — Faye Boosalis
(74) *Attorney, Agent, or Firm* — Wolf, Greenfield & Sacks, P.C.

(57) ABSTRACT

A method of setting a laser-light intensity value includes: emitting laser light, the laser light being excitation light, a fluorescent-dyed biological sample being irradiated with the excitation light and emitting light; detecting fluorescence emitted by the biological sample, and outputting a signal corresponding to a brightness value; prestoring relation information, the relation information including the plurality of laser-light intensity values, and information on at least one possible correlation between a phototoxicity degree and the brightness value in relation to each of the laser-light intensity values, the phototoxicity to the biological sample resulting from the laser light; generating a fluorescence image having the brightness value based on the output signal; calculating a brightness value representative of a ROI area based on the generated fluorescence image; and referring to the relation information, and determining a laser-light intensity value satisfying tolerance of the phototoxicity based on the calculated representative brightness value.

6 Claims, 10 Drawing Sheets

| Image-taking setting information | Purpose |
|---|---|
| Laser-wavelength information | Sort attenuation level depending on wavelength |
| Image-taking time | Predict maximum fluorescence-observation time period |
| Microscope-type information | Select table |
| Position-in-Z-direction | Control laser-light intensity based on depth |
| Photodetector sensitivity | Control dynamic range |

FIG.2

| User-input information | Purpose |
|---|---|
| Observed object (cell, cranial nerve) | Select table |
| Fluorescent dye (DAPI, CFP, GFP···) | Select table |
| Purpose of measurement (fluorescence lifetime, FRET, calcium imaging) | Necessity of controlling laser-light intensity value |

FIG.3

|  | Wavelength | Fluorescent reagent | Laser-light intensity value |
|---|---|---|---|
| UV | 390nm | DAPI | 10mW |
| BLUE | 438nm | CFP | 20mW |
| GREEN | 542nm | TRITC/Cy3 | 20mW |
| YELLOW | 575nm | TexasRed | 30mW |
| RED | 632nm | Cy5 | 40mW |

FIG.5

LASER SCANNING MICROSCOPE SYSTEM AND METHOD OF SETTING LASER-LIGHT INTENSITY VALUE

CROSS REFERENCE TO RELATED APPLICATIONS

This application claims the benefit of Japanese Priority Patent Application JP 2013-221363 filed Oct. 24, 2013, the entire contents of which are incorporated herein by reference.

BACKGROUND

The present disclosure relates to a laser scanning microscope system and a method of setting a laser-light intensity value in view of cell phototoxicity and fluorescence fading.

In recent years, laser microscopes such as confocal microscopes and multiphoton excitation microscopes are designed in various ways to control intensity values of emission from laser light sources, in order to reduce phototoxic damages to samples such as cells.

For example, according to the technology disclosed in Japanese Patent Application Laid-open No. 2012-212133, sectional images of a sample is obtained in order from the surface of the sample in the depth direction. A laser-light intensity value is controlled based on the fluorescence distribution of those sectional images. In other words, the laser-light intensity value is controlled based on the depth from the surface of the sample. As a result, according to this document, fluorescence images may not be affected by scattering and the like resulting from the thickness of the sample, and fluorescence images having the same brightness may be obtained.

Moreover, when a fluorescent-dyed sample is observed, a fluorescent material is excited and fading of fluorescence occurs as a result, which is problematic. For example, the technology disclosed in Japanese Patent Application Laid-open No. 2012-128354 deals with the fading problem. According to this technology, in order to deal with fluorescence fading, when a plurality of images are taken, the laser-light intensity value is changed from a high intensity value to a low intensity value, and the sensitivity of a photodetector is changed from high sensitivity to low sensitivity. A high laser-light intensity value and high sensitivity are selected before fluorescence is faded, and then an image is taken. As a result, an image of a low brightness area of a cell, i.e., a sample, may be taken sharply. According to this technology, a plurality of images having different fluorescence intensity values are taken, and those images are synthesized. As a result, a synthesized image having a large dynamic range may be obtained.

SUMMARY

According to the technology of Japanese Patent Application Laid-open No. 2012-212133, a laser-light intensity value is decreased in order to take a sharp image of a section close to the surface of a sample, for example. This technology does not directly concern phototoxicity. Moreover, the technology of Japanese Patent Application Laid-open No. 2012-128354 does not deal with a fluorescence-fading phenomenon resulting from irradiation with laser light, per se.

In view of this, it is desirable to variously modify laser scanning microscope systems in order to take images efficiently.

In view of the above-mentioned circumstances, it is desirable to provide a laser scanning microscope system and a method of setting laser-light intensity value capable of taking images efficiently.

According to an embodiment of the present disclosure, there is provided a laser scanning microscope system, including: a laser light source capable of emitting laser light, the laser light being excitation light, a fluorescent-dyed biological sample being irradiated with the excitation light and emitting light; a photodetector configured to detect fluorescence emitted by the biological sample, and to output a signal corresponding to a brightness value; and a controller apparatus including storage configured to prestore first relation information, the first relation information including the plurality of laser-light intensity values, and information on at least one possible correlation between a phototoxicity degree and the brightness value in relation to each of the laser-light intensity values, the phototoxicity to the biological sample resulting from the laser light, and a controller configured to generate a fluorescence image having the brightness value based on the signal output from the photodetector, to calculate a brightness value representative of a ROI area based on the generated fluorescence image, and to refer to the first relation information, and to determine a laser-light intensity value satisfying tolerance of the phototoxicity based on the calculated representative brightness value.

According to an embodiment of the present disclosure, the storage may be configured to further prestore second relation information, the second relation information including the plurality of laser-light intensity values, and information on at least one possible correlation between a fading degree of the fluorescence and the brightness value in relation to each of the laser-light intensity values, the fading of the fluorescence of the biological sample resulting from the laser light, and the controller is configured to select, based on the calculated representative brightness value, one of a laser-light intensity value satisfying a tolerance of the phototoxicity determined with reference to the first relation information and a laser-light intensity value satisfying a tolerance of the fading determined with reference to the second relation information, the selected laser-light intensity value being smaller than the other laser-light intensity value.

According to an embodiment of the present disclosure, the storage may be configured to prestore third relation information, the third relation information showing a relation between a depth and an attenuation degree of the excitation light, the depth being between a surface of the biological sample and a position irradiated with the excitation light, and the controller is configured to refer to the third relation information, and to correct the selected laser-light intensity value.

According to an embodiment of the present disclosure, the controller may be configured to select sensitivity of the photodetector based on the corrected laser-light intensity value.

According to an embodiment of the present disclosure, the storage may be configured to prestore fourth relation information, the fourth relation information showing relation between an elapsed time of observation of the biological sample and a laser-light intensity value satisfying a tolerance of phototoxicity, the phototoxicity to the biological sample resulting from the laser light, and the controller is configured to select one of the corrected laser-light intensity value and a laser-light intensity value determined based on the elapsed time of observation with reference to the fourth relation information, the selected laser-light intensity value being lower than the other laser-light intensity value.

According to an embodiment of the present disclosure, the storage may be configured to prestore fifth relation information, the fifth relation information showing relation between an elapsed time of observation of the biological sample and a laser-light intensity value satisfying a tolerance of fading, the fading being given to the biological sample by the laser light, and the controller is configured to select one of the corrected laser-light intensity value and a laser-light intensity value determined based on the elapsed time of observation with reference to the fifth relation information, the selected laser-light intensity value being lower than the other laser-light intensity value.

According to an embodiment of the present disclosure, there is provided a method of setting a laser-light intensity value, including: emitting laser light, the laser light being excitation light, a fluorescent-dyed biological sample being irradiated with the excitation light and emitting light; detecting fluorescence emitted by the biological sample, and outputting a signal corresponding to a brightness value; prestoring relation information, the relation information including the plurality of laser-light intensity values, and information on at least one possible correlation between a phototoxicity degree and the brightness value in relation to each of the laser-light intensity values, the phototoxicity to the biological sample resulting from the laser light; generating a fluorescence image having the brightness value based on the output signal; calculating a brightness value representative of a ROI area based on the generated fluorescence image; and referring to the relation information, and determining a laser-light intensity value satisfying tolerance of the phototoxicity based on the calculated representative brightness value.

As described above, according to the present technology, it is possible to take an image efficiently in view of cell phototoxicity and fluorescence fading resulting from irradiation with laser light.

Note that in addition to the above-mentioned effect, any effect described in the present disclosure may be obtained.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 2 shows specific examples of setting information (image-taking setting information) used to take an image, and purposes of the image-taking setting information;

FIG. 3 shows specific examples of information (user-input information) on a sample input by a user, who performs fluorescence observation, and purposes of the user-input information;

FIG. 5 is a table showing appropriate laser-light intensity values depending on combinations of wavelengths of laser light and the kinds of fluorescent reagents;

FIG. 9 is a diagram schematically showing the configuration of the microscope system 1a;

DETAILED DESCRIPTION OF EMBODIMENTS

Hereinafter, embodiments of the present disclosure will be described with reference to the drawings. Note that hereinafter a confocal microscope, i.e., one kind of fluorescence microscopes, will be described as an example. Note that it does not mean that the present technology is only applicable to confocal microscopes. As a matter of course, the present technology is applicable to other microscopes, for example, multiphoton microscopes or the like.

First Embodiment

[Configuration of Microscope System]

Figure 1:
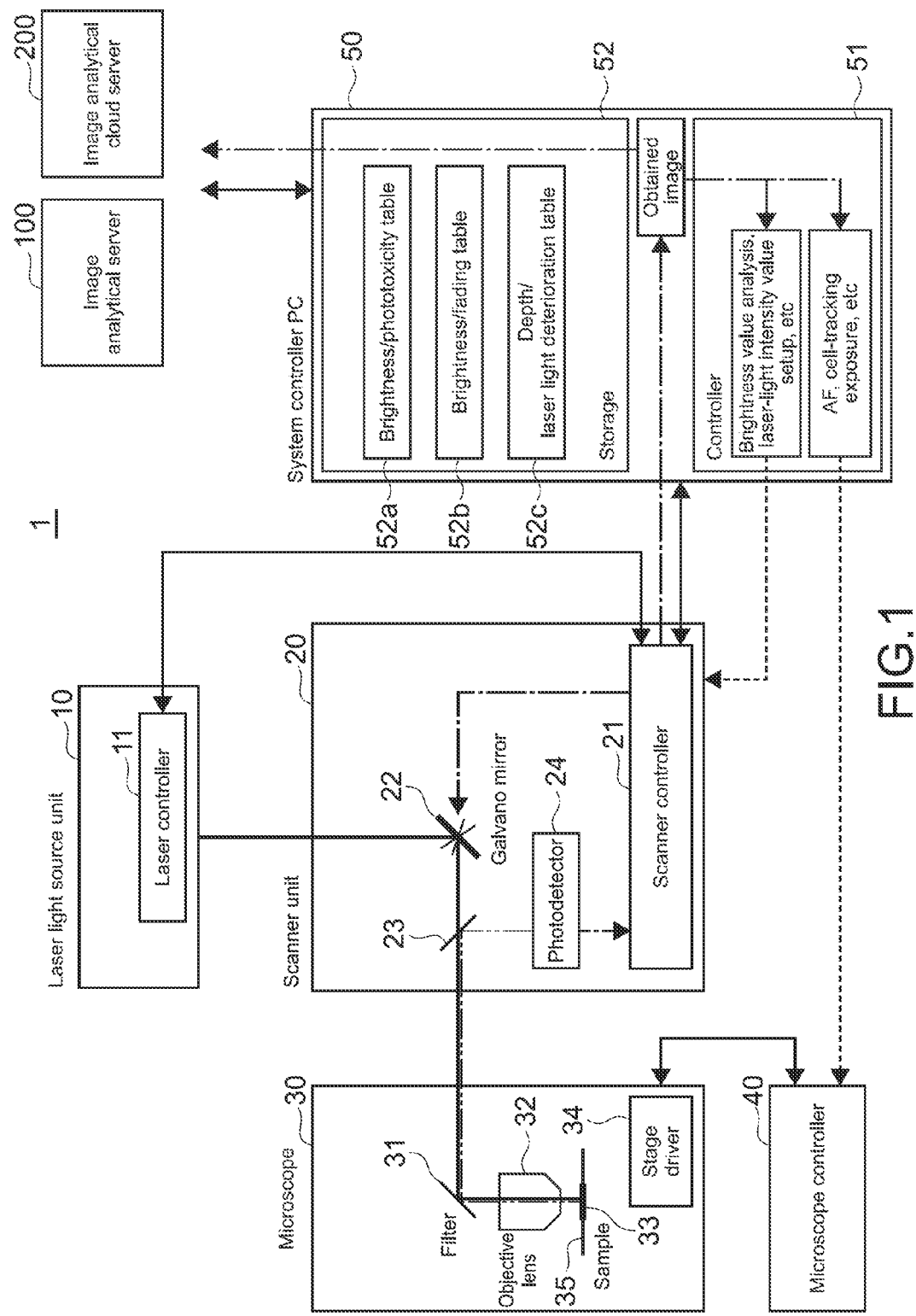
FIG. 1 is a diagram schematically showing the configuration of the microscope system 1.

Firstly, a microscope system 1 of the present technology will be described schematically. Note that the microscope system 1 is a laser scanning microscope system. FIG. 1 is a diagram schematically showing the configuration of the microscope system 1.

The microscope system 1 includes a laser light source unit (laser light source) 10, a scanner unit 20, a microscope 30, a microscope controller 40, and a system controller PC (Personal Computer) (controller) 50. Note that the system controller PC 50 analyzes images and performs other processing. Alternatively, an image analytical server 100 in a local network or an image analytical cloud server 200 in the Internet cloud may analyze images and perform other processing.

The laser light source unit 10 generates excitation light such that a sample (biological sample) such as a fluorescently-labeled cell may generate fluorescence. The generated excitation light enters the scanner unit 20.

The laser light source unit 10 includes a laser controller 11. The laser controller 11 controls intensity values of the excitation light, light-emitting intervals, and the like. In this embodiment, the system controller PC 50 determines laser-light intensity values. The system controller PC 50 notifies the laser controller 11 of the determined laser-light intensity value via a scanner controller (described later).

The scanner unit 20 includes a scanner controller 21, a galvano mirror 22, a dichroic mirror 23, and a photodetector 24.

The galvano mirror 22 changes directions of laser light such that the laser-light scanning is performed in the X direction and the Y direction. As a result, the excitation laser light introduced from the laser light source unit 10 moves in the horizontal direction (XY directions) of a sample, which is mounted on the stage 35 of the microscope 30, and the sample is irradiated with the excitation laser light. The laser light, whose direction is controlled by the galvano mirror 22, passes through the dichroic mirror 23. Then the laser light enters the microscope 30. The sample is irradiated with the laser light entered in the microscope 30. When the sample is irradiated with the laser light, the sample is excited and generates fluorescence. The fluorescence returns from the microscope 30 to the scanner unit 20.

The laser light and the fluorescence return from the microscope 30 to the dichroic mirror 23. The dichroic mirror 23 reflects only the fluorescence out of them to the photodetector 24.

Generally, the photodetector 24 is a PMT (photomultiplier tube). As described above, when the sample is irradiated with the laser light, the sample is excited and generates fluorescence. The photodetector 24 detects the fluorescence. Note that in a confocal microscope, a pinhole is provided on the light path in front of the photodetector 24. There is a conjugate relation between the position of the pinhole and the focal position of the objective lens 32 (described later).

The scanner controller 21 controls the galvano mirror 22 and controls the photodetector 24 to scan the sample in the XY directions. The scanner controller 21 converts the signals, which are detected by the photodetector 24, to brightness values of the respective points on the scanned XY plane. The scanner controller 21 transmits the brightness values to the system controller PC 50.

The microscope 30 includes a filter 31, the objective lens 32, the stage 35, and a stage driver 34. Note that a sample is mounted on the stage 35, and is observed.

The filter 31 guides the laser light entered from the scanner unit 20 to the objective lens 32. Moreover, the sample is irradiated with the laser, and generates fluorescence. The filter 31 guides the fluorescence to the scanner unit 20.

The objective lens 32 collects the laser light, which enters from the scanner unit 20 via the filter 31, on the focal position of the objective lens 32. Moreover, the objective lens 32 guides the fluorescence, which is generated by the sample, to the scanner unit 20 via the filter 31.

A sample is mounted on the stage 35. The stage driver 34 moves the stage 35 in the XY directions and in the Z direction. The XY directions are orthogonal to the optical axis of the objective lens 32. The Z direction is along the optical axis of the objective lens 32.

The system controller PC 50 inputs instructions on autofocus, cell-tracking exposure, and the like in the microscope controller 40. The microscope controller 40 outputs instructions for moving the stage 35 to the stage driver 34 based on the instructions from the system controller PC 50.

The system controller PC 50 includes a controller 51 and storage 52.

The controller 51 controls the entire microscope system 1. The controller 51 synthesizes a fluorescence image based on the brightness values detected by the photodetector 24 and based on the coordinate values on the XY plane of the detected brightness values. The controller 51 analyzes the synthesized fluorescence image, calculates the optimum laser-light intensity value, and controls the laser-light intensity value. Moreover, as described above, the controller 51 controls the microscope controller 40, and causes the autofocus function to perform the cell-tracking exposure function, and the other functions of the microscope 30. Note that a CPU (Central Processing Unit) executes programs stored in the storage 52 to implement the controller 51.

The storage 52 includes a hard disk drive and/or a semiconductor memory. The storage 52 stores the above-mentioned programs executed by the CPU, and the fluorescence image obtained by the scanner unit 20. The storage 52 further stores brightness/phototoxicity tables 52a (first relation information, relation information), brightness/fading tables 52b (second relation information), depth/laser light deterioration tables 52c (third relation information), and the like. The three kinds of tables stored in the storage 52, i.e., the brightness/phototoxicity tables 52a, the brightness/fading tables 52b, and the depth/laser light deterioration tables 52c, will be described later.

The configuration of the microscope system 1 has been described schematically.

[Three Kinds of Tables]

Here, the above-mentioned three kinds of tables will be described. Those tables relate to the basic mechanism of the present technology.

According to the basic mechanism of the present technology, firstly, a fluorescence image is taken. The current phototoxicity and the current fading degree are determined based on the brightness value of a ROI (Region Of Interest) area in the taken fluorescence image. The laser-light intensity value is controlled such that the determined phototoxicity and fading degree may not affect observation. Then another image is taken with the controlled laser light.

Note that, for example, a taken and synthesized fluorescence image has thirty-two blocks in a matrix. The above-mentioned ROI area is a block, which has many large brightness values (large brightness density) out of the thirty-two blocks. In the present technology, a laser-light intensity value is controlled based on the brightness value representative of the ROI area. The brightness value representative of the ROI area may be a dynamic range value of the ROI area.

It is necessary to previously measure relations between fluorescence intensity values (brightness values) and phototoxicity degrees/fluorescence fading degrees obtained by using various kinds of laser light having various intensity values. Those relations are measured in relation to combinations of cells (samples) to be observed and fluorescent reagents to be used for observation. After that, as described above, the current phototoxicity and the current fading degree are determined based on a brightness value. As described above, pieces of data on various combinations of cells and fluorescent reagents are collected. This is because the fluorescence intensity values, phototoxicity degrees, and fading degrees to be obtained are different depending combinations.

The above-mentioned brightness/phototoxicity table 52a shows the relation between brightness values and phototoxicity measured for each laser-light intensity value, as described above.

Moreover, similarly, the above-mentioned brightness/fading table 52b shows the relation between brightness values and fading measured for each laser-light intensity value. The brightness/fading table 52b is also generated for each kind of fluorescent reagents.

Note that attenuation of laser light depending on depth is measured. The depth is between a surface of a sample, which is irradiated with laser light, and an observed point. The depth/laser light deterioration table 52c shows data on the attenuation of laser light relative to the depth.

Those tables are generated in relation to laser-light intensity values, the kinds of fluorescent reagents, and the kinds of samples. So a huge number of tables are generated.

A phototoxicity degree, a fading degree, and a laser light deterioration degree are obtained based on a brightness value with reference to the three kinds of tables. Hereinafter, the phototoxicity degree, the fading degree, and the laser light deterioration degree will be referred to as a phototoxicity parameter, a fading parameter, and a laser-light deterioration parameter, respectively.

Note that, in the above description, the tables show the relation between brightness values and phototoxicity, the relation between brightness values and fading, and the relation between brightness values and depth. Alternatively, if possible, functions showing those relations may be prepared. In the case where functions showing those relations are prepared, the storage 52 stores function-formulae instead of the above-mentioned tables.

The three kinds of tables have been described.

[Processing Flow]

In this embodiment, the processing flow roughly includes the initial setting process and the main image-taking process. The initial setting process is performed only once before the main image-taking process. The main image-taking process is performed again and again while brightness values are fed back and the laser-light intensity value is controlled.

In the following description of the processing, firstly, information collected in the initial setting process will be described. After that, the entire processing flow will be described.

(Information Collected in Initial Setting Process)

The controller 51 collects information during the initial setting process. Here, the information collected by the controller 51 will be described in detail. The collected information is used in the main image-taking process. For example, the collected information is used to select a laser-light intensity value to take an image for the first time.

FIG. 2 shows specific examples of setting information (image-taking setting information) used to take an image, and purposes of the image-taking setting information. Moreover, FIG. 3 shows specific examples of information (user-input information) on a sample input by a user, who performs fluorescence observation, and purposes of the user-input information.

Firstly, laser-wavelength information is one piece of image-taking setting information. For example, the above-mentioned three kinds of tables may be generated in relation to laser-light intensity values and, in addition, laser wavelengths. In this case, the laser-wavelength information is used as a reference to select one of the tables in relation to laser wavelengths. Note that the tables in relation to laser wavelengths are used to sort attenuation levels of laser light.

Next, image-taking time information is another piece of image-taking setting information. The image-taking time information is used to predict a maximum time period in which fluorescence observation is performed.

Next, microscope-type information is another piece of image-taking setting information. The microscope-type information distinguishes between a confocal microscope and a multiphoton microscope, which takes a fluorescence image. Such distinction is used to set a laser-light intensity value because the phototoxicity of the confocal microscope is larger than the phototoxicity of the multiphoton microscope.

Next, position-in-Z-direction information is another piece of image-taking setting information. The position-in-Z-direction information is used to control a laser-light intensity value based on the depth between a sample surface and observed position.

Next, photodetector sensitivity information is another piece of image-taking setting information. The photodetector sensitivity information is used to appropriately control a dynamic range when taking an image.

Note that the above-mentioned pieces of image-taking setting information are necessary when taking an image except for the image-taking time information. So those pieces of image-taking setting information may be obtained without fail before the main image-taking process.

Next, description will be made with reference to FIG. 3. Firstly, observed-object information is one piece of user-input information of FIG. 3. The observed-object information is used to select some of the above-mentioned tables. The reason is as follows. The laser-light intensity value to be selected is different depending on the kind of a sample, i.e., a general cell or a special nerve cell, for example. Note that one brightness/phototoxicity table 52a and one depth/laser light deterioration table 52c are selected.

Next, fluorescent-dye information is another piece of user-input information. Examples of fluorescent dye (fluorescent reagent) include, for example, DAPI (4',6-diamidino-2-phenylindole), CFP (Cyan Fluorescent Protein), GFP (Green Fluorescent Protein), and the like. The fluorescent-dye information is used to select one appropriate brightness/fading table 52b.

Next, purpose-of-measurement information is another piece of user-input information. The purpose-of-measurement information shows purpose of observation. Examples of the purpose of observation include measurement of a fluorescence lifetime, measurement of FRET (Fluorescence resonance energy transfer), calcium imaging, and the like. The purpose-of-measurement information is used to determine if a laser-light intensity value is to be controlled or not in the main image-taking process. For example, in the case of measuring a fluorescence lifetime, a laser-light intensity value should not be controlled but should be constant.

The image-taking setting information and the user-input information, which are collected in the initial setting process, have been described in detail.

(Flow of Entire Processing)

Figure 4:
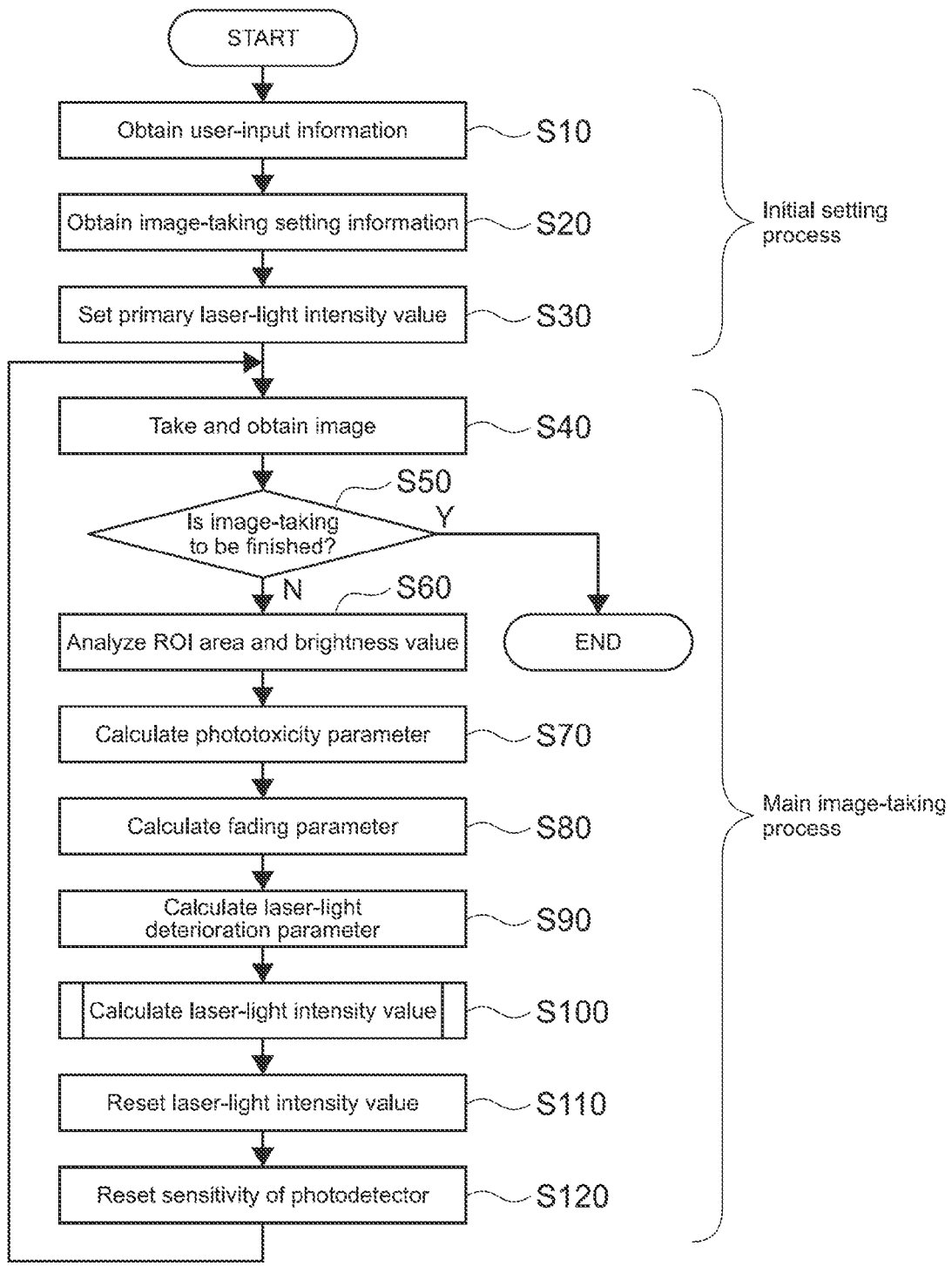
FIG. 4 is a flowchart illustrating the flow of entire processing performed by the controller 51 of the system controller PC 50.

Here, the flow of entire processing performed by the controller 51 of the system controller PC 50 will be described. FIG. 4 is a flowchart illustrating the flow of entire processing performed by the controller 51 of the system controller PC 50.

Firstly, the controller 51 obtains user-input information (Step S10). The user-input information has been described in detail.

Next, the controller 51 obtains image-taking setting information (Step S20). The image-taking setting information has been described in detail.

Next, the controller 51 determines a primary laser-light intensity value to take a fluorescence image for the first time based on the obtained user-input information and the obtained image-taking setting information. Then the determined primary laser-light intensity value is set for the laser controller 11 (Step S30).

The initial setting process includes the process of Step S10 to Step S30. The main image-taking process includes the process of Step S40 and thereafter.

Next, the controller 51 inputs instructions for taking a fluorescence image of a sample in the laser controller 11, the scanner controller 21, and the microscope controller 40. The controller 51 obtains a taken fluorescence image (Step S40).

Next, the controller 51 determines if image-taking is to be finished or not (Step S50).

If image-taking is not to be finished (Step S50, N), next, the controller 51 analyzes the obtained fluorescence image. The controller 51 selects an ROI area, and calculates a brightness value representative of the ROI area (Step S60).

Next, the controller 51 calculates a phototoxicity parameter (laser-light intensity value) based on the calculated brightness value and based on a brightness/phototoxicity table 52a stored in the storage 52 (Step S70).

Next, the controller 51 calculates a fading parameter (laser-light intensity value) based on the calculated brightness value and based on a brightness/fading table 52b stored in the storage 52 (Step S80).

The depth between the sample surface and the measured point is calculated based on the obtained position-in-Z-direction information by using a generally-known method. Next, the controller 51 calculates a laser-light deterioration parameter based on the depth and based on a depth/laser light deterioration table 52c stored in the storage 52 (Step S90).

Next, the controller 51 calculates a laser-light intensity value, which is to be used when taking a next image, based on the phototoxicity parameter, the fading parameter, and the laser-light deterioration parameter (Step S100). Note that the method of calculating a laser-light intensity value based on the phototoxicity parameter, the fading parameter, and the laser-light deterioration parameter will be described later in detail.

Next, the controller 51 resets a laser-light intensity value for taking an image with the calculated laser-light intensity value for the laser controller 11 (Step S110). Because the laser-light intensity value is controlled here, it is possible to prevent the saturation of a fluorescence image from being increased and to use a dynamic range effectively.

Next, the controller 51 predicts a fluorescence intensity value such that the optimum dynamic range may be obtained in combination with the reset laser-light intensity value. The controller 51 also resets the sensitivity of the photodetector 24 (Step S120).

After the process of Step S120, the controller 51 returns to Step S40, and takes an image of a sample based on the reset laser-light intensity value and the reset sensitivity.

Note that in the above-mentioned Step S30, a primary laser-light intensity value, which is used to take a fluorescence image for the first time, is determined based on the obtained user-input information and the obtained image-taking setting information. At this time, as shown in FIG. 5, there may be prepared a table showing appropriate laser-light intensity values depending on combinations of wavelengths of laser light and the kinds of fluorescent reagents. A laser-light intensity value in the table, which satisfies a condition, may be a primary laser-light intensity value.

The entire processing flow of the controller 51 of the system controller PC 50 has been described.

(Method of Calculating Laser-Light Intensity Value)

Figure 6:
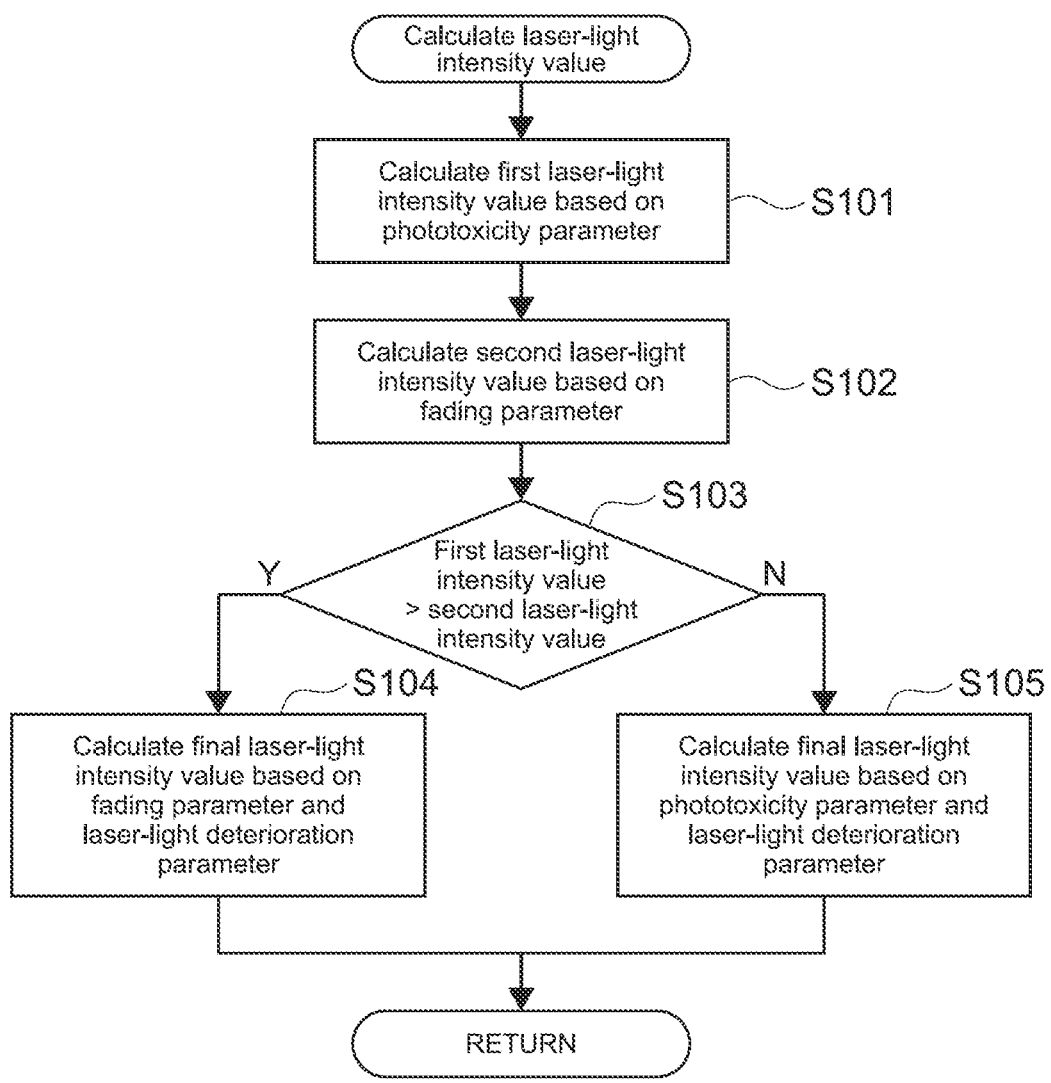
FIG. 6 is a flowchart illustrating the method of calculating a laser-light intensity value.

Here, the method of calculating a laser-light intensity value of the above-mentioned Step S100 will be described. FIG. 6 is a flowchart illustrating the method of calculating a laser-light intensity value.

Note that, in the method described below, one of the cell phototoxicity parameter and the fluorescence fading parameter having a larger influence is selected. A laser-light intensity value is calculated based on the selected parameter. Here, the parameter having a larger influence is selected as follows. For example, the parameter exhibiting the smaller laser-light intensity value is selected.

Note that the influence of the cell phototoxicity parameter is compared with the influence of the fluorescence fading parameter as follows. In the following, the laser-light intensity value (laser-light intensity value satisfying tolerance of phototoxicity) required to reduce the phototoxicity is compared with the laser-light intensity value (laser-light intensity value satisfying tolerance of fading) required to reduce fading.

Then, a parameter requiring a smaller laser-light intensity value is selected. Then, a final laser-light intensity value used for resetting is calculated based on the selected parameter and a laser-light deterioration parameter.

Such a calculation method is used because it is necessary to determine a laser-light intensity value to reduce influence of phototoxicity, to reduce influence of fading, and to make an observation time longer. The criterion for calculating a laser-light intensity value to be reset is changed depending on the cell phototoxicity parameter or the fluorescence fading parameter, which has a larger impact on a sample to be observed.

Firstly, the controller 51 obtains a first laser-light intensity value based on the phototoxicity parameter calculated in Step S70 (Step S101).

Next, the controller 51 obtains a second laser-light intensity value based on the fading parameter calculated in Step S80 (Step S102).

Next, the controller 51 determines if the first laser-light intensity value is larger than the second laser-light intensity value or not (Step S103).

The controller 51 gives priority to the smaller laser-light intensity value, and calculates a final laser-light intensity value based on the smaller laser-light intensity value. So if the first laser-light intensity value is larger than the second laser-light intensity value (Step S103, Y), the controller 51 selects the fading parameter. Then, the controller 51 calculates a final laser-light intensity value used for resetting based on the selected fading parameter and the laser-light deterioration parameter (Step S104).

The final laser-light intensity value is obtained based on the following formula, where 1roi is a brightness value representative of the ROI area, Sf( ) is a fading parameter, z is the depth between a sample surface and an observed position, and D( ) is a laser-light deterioration parameter.

$$\text{Final laser-light intensity value} = Sf(1roi) \times D(z) \tag{1}$$

The controller 51 gives priority to the smaller laser-light intensity value, and calculates a final laser-light intensity value based on the smaller laser-light intensity value. To the contrary, if the first laser-light intensity value is not larger than the second laser-light intensity value (Step S103, N), the controller 51 selects the phototoxicity parameter. Then, the controller 51 calculates a final laser-light intensity value used for resetting based on the selected phototoxicity parameter and the laser-light deterioration parameter (Step S105).

The final laser-light intensity value is obtained based on the following formula, where 1roi is a brightness value representative of the ROI area, Sp( ) is a phototoxicity parameter, z is the depth between a sample surface and an observed position, and D( ) is a laser-light deterioration parameter.

$$\text{Final laser-light intensity value} = Sp(1roi) \times D(z) \tag{2}$$

Note that a final laser-light intensity value used for resetting may be calculated as follows. The phototoxicity parameter or the fading parameter is multiplied by the laser-light deterioration parameter. The phototoxicity parameter or the fading parameter multiplied by the laser-light deterioration parameter corresponds to the phototoxicity or the fading status biased in the depth direction.

The method of calculating a laser-light intensity value in the above-mentioned Step S100 has been described.

[Concept of Laser-Light Intensity Value Control]

Figure 7:
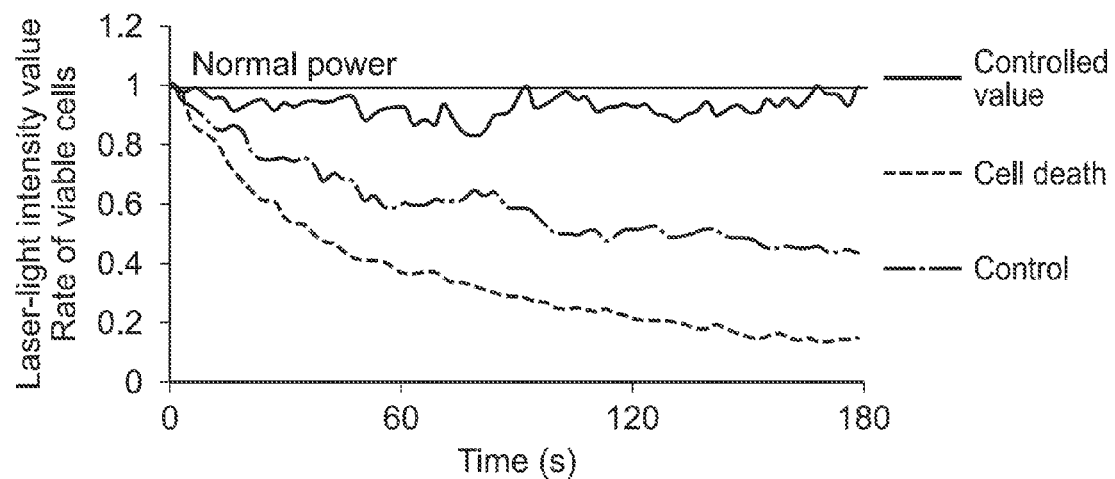
FIG. 7 is a diagram illustrating the concept of control of cell death resulting from phototoxicity, in which the laser-light intensity value is controlled.

Here, the concept of control of cell death in relation to phototoxicity by controlling the above-mentioned laser-light intensity value will be described. FIG. 7 is a diagram illustrating the concept of control of cell death resulting from phototoxicity, in which the laser-light intensity value is controlled.

In the graph of FIG. 7, the horizontal axis shows observation time (second). Moreover, the vertical axis shows relative laser-light intensity values, where the normal laser-light intensity value is 1. The vertical axis further shows the relative rate of viable cells, where the number of viable cells at the start of observation is 1.

Firstly, the laser-light intensity value of the normal power, i.e., 1, is maintained (straight line of "normal power" in graph), and cells are observed. In this case, the line "cell death" shows how the rate of viable cells changes as time passes.

The line "cell death" shows the following fact. When the laser-light intensity value is constant, the rate of viable cells falls below 0.5 after sixty seconds, for example. Then, the viable cell rate is decreased after that.

To the contrary, the laser-light intensity value is controlled as time passes, and the line "control" of the graph shows the laser-light intensity values. In this case, the "controlled value" of the graph shows that cell death is prevented from occurring, and the viable cell rate is not decreased.

Note that fluorescence fading is controlled similar to the graph of phototoxicity.

The concept of control of cell death in relation to phototoxicity by controlling the laser-light intensity value has been described.

[Outline of this Embodiment]

The outline of this embodiment is as follows. In other words, according to this embodiment, the laser scanning microscope system 1 includes: the laser light source unit 10 capable of emitting laser light, the laser light being excitation light, a fluorescent-dyed biological sample being irradiated with the excitation light and emitting light; the photodetector 24 configured to detect fluorescence emitted by the biological sample, and to output a signal corresponding to a brightness value; and the system controller PC 50 including the storage 52 configured to prestore first relation information, the first relation information including the plurality of laser-light intensity values, and information on at least one possible correlation between a phototoxicity degree and the brightness value in relation to each of the laser-light intensity values, the phototoxicity to the biological sample resulting from the laser light, and the controller configured to generate a fluorescence image having the brightness value based on the signal output from the photodetector 24, to calculate a brightness value representative of a ROI area based on the generated fluorescence image, and to refer to the first relation information, and to determine a laser-light intensity value satisfying tolerance of the phototoxicity based on the calculated representative brightness value.

Second Embodiment

Next, the second embodiment will be described. In the first embodiment, image-taking setting information and user-input information are obtained to set a primary laser-light intensity value. To the contrary, in this embodiment, a primary laser-light intensity value is selected without obtaining user-input information. Because user-input information is not obtained, the process may be performed more automatically.

Note that in this embodiment, instead of obtaining user-input information, a low laser-light intensity value is set, and an image of a sample is taken preliminarily. Then, the preliminarily-taken fluorescence image is recognized. As a result, information corresponding to the user-input information is obtained.

[Configuration of Microscope System]

The configuration of the microscope system of the second embodiment is similar to the configuration of the microscope system 1 of the first embodiment. The configuration of the microscope system of the second embodiment will thus not be described. The configuration of the microscope system of the second embodiment is different from that of the first embodiment in that the controller 51 of the system controller PC 50 preliminarily takes an image of a sample and recognizes the preliminarily-taken fluorescence image.

Note that similar to the first embodiment, not the controller 51 but the image analytical server 100 in the local network or the image analytical cloud server 200 in the Internet cloud may recognize the image.

The configuration of the microscope system 1 has been described above.

[Processing Flow]

The processing flow of this embodiment roughly includes the preliminary image-taking process and the main image-taking process. The preliminary image-taking process is performed only once before the main image-taking process. The main image-taking process is similar to that of the first embodiment. The main image-taking process is performed again and again while brightness values are fed back and the laser-light intensity value is controlled.

In the following description of the processing, firstly, information collected in the preliminary image-taking process will be described. After that, the part of the entire processing flow different from the first embodiment will be described.

(Information Collected in Preliminary Image-Taking Process)

The controller 51 collects information during the preliminary image-taking process. Here, the information collected by the controller 51 will be described in detail. The controller 51 collects the image-taking setting information same as that of the first embodiment, laser-light intensity value information at the time of preliminary image-taking, and a preliminarily-taken fluorescence image.

The image-taking setting information, the laser-light intensity value information at the time of preliminary image-taking, and the preliminarily-taken fluorescence image are used to recognize an image after the image is taken preliminarily, and to select a laser-light intensity value to take an image for the first time in the main image-taking process, for example.

(Processing Flow (Different Part))

Figure 8:
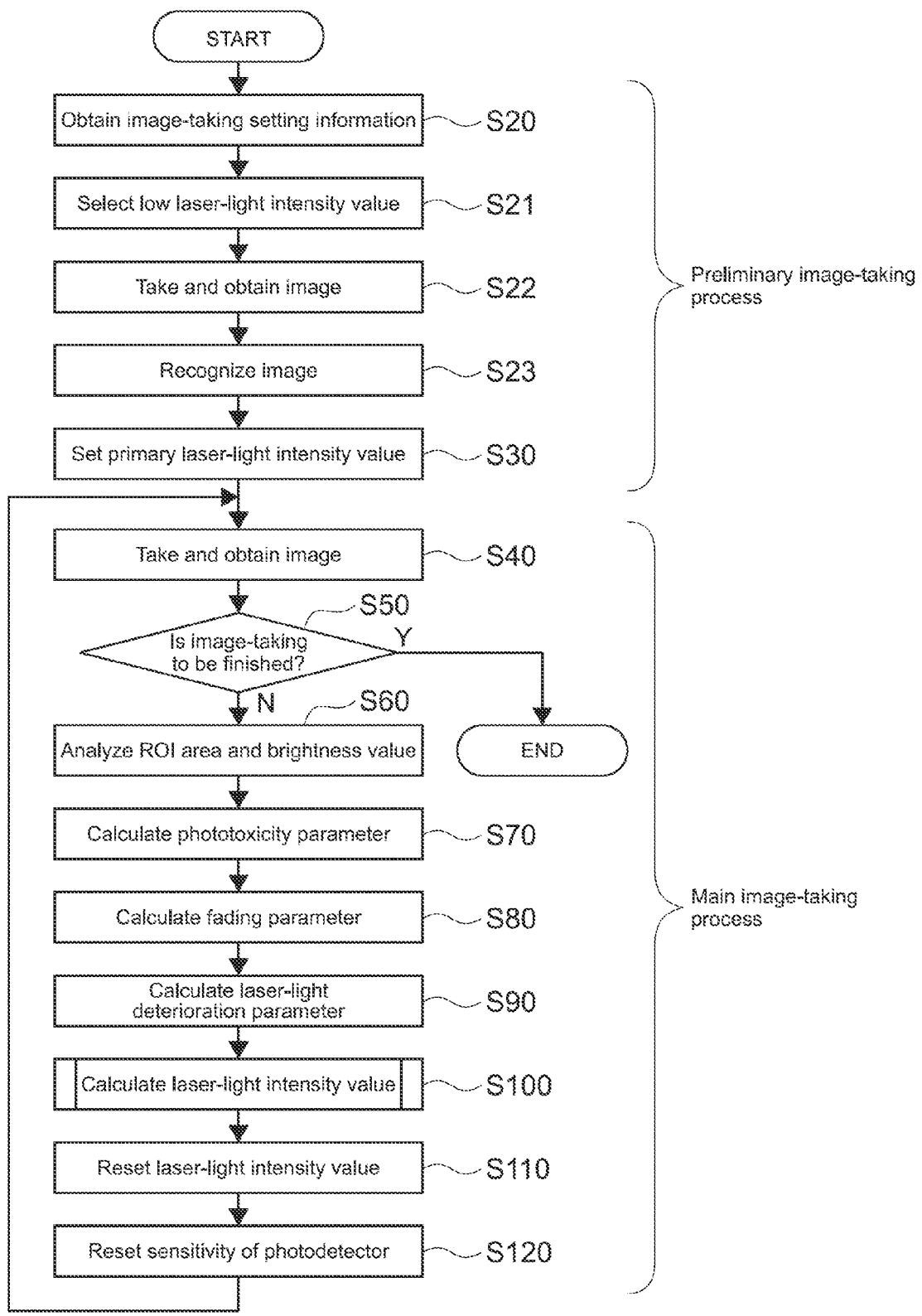
FIG. 8 is a flowchart illustrating the entire processing flow of the controller 51 of the system controller PC 50.

Here, part of the entire processing flow of the controller 51 of the system controller PC 50, which is different from that of the first embodiment, will be described. FIG. 8 is a flowchart illustrating the entire processing flow of the controller 51 of the system controller PC 50.

First, the controller 51 obtains image-taking setting information (Step S20). The image-taking setting information has been described in detail.

Next, the controller 51 selects a low laser-light intensity value for preliminary image-taking (Step S21). The laser-light intensity value may be such a value that information corresponding to the user-input information may be obtained by recognizing a taken fluorescence image of a sample.

Next, the controller 51 inputs instructions for taking a fluorescence image of a sample in the laser controller 11, the scanner controller 21, and the microscope controller 40. The controller 51 obtains a taken fluorescence image (Step S22).

Next, the controller 51 recognizes the fluorescence image preliminarily taken in Step S22 (Step S23). The image is recognized based on a known general method.

For example, a plurality of samples to be observed are dyed with various fluorescent reagents to be used for observation, and many fluorescence images are obtained previously. In the image recognition process, the preliminarily-taken image is compared with those previously obtained images. Information corresponding to the user-input information is presumed based on the result. In other words, the kind of the sample of the taken fluorescence image, the kind of the used fluorescent reagent, and the purpose of observation are presumed.

Next, the controller 51 determines the primary laser-light intensity value for the main image-taking process based on the obtained image-taking setting information and based on the presumed user-input information. Then the determined primary laser-light intensity value is set for the laser controller 11 (Step S30).

The preliminarily image-taking process is different from the process of the first embodiment and has been described above. The process after that is the same as the process of the first embodiment, and description thereof will be omitted.

The part of the entire processing flow of the controller 51 of the system controller PC 50, which is different from that of the first embodiment, has been described.

Third Embodiment

In the above-mentioned embodiments, a brightness value of a taken fluorescence image is fed back. A phototoxicity status of a sample and a fluorescence fading status are obtained based on the brightness value. Then a laser-light intensity value, which is to be used to take a next image, is controlled. To the contrary, in this embodiment, an elapsed time of observation is also fed back in addition to the brightness value. As a result, accuracy of controlling laser light may be improved.

Note that the graph (FIG. 7) of the first embodiment is used to feed back an elapsed time and to reflect the elapsed time in a laser-light intensity value. An elapsed time is obtained. A relative laser-light intensity value of the line "control" at the obtained elapsed time is used. As a result, it is possible to control a laser-light intensity value in view of the phototoxicity. The same is applied to fluorescence fading.

Note that the part different from the first embodiment will only be described hereinafter based on the first embodiment.

[Configuration of Microscope System]

Figure 9:
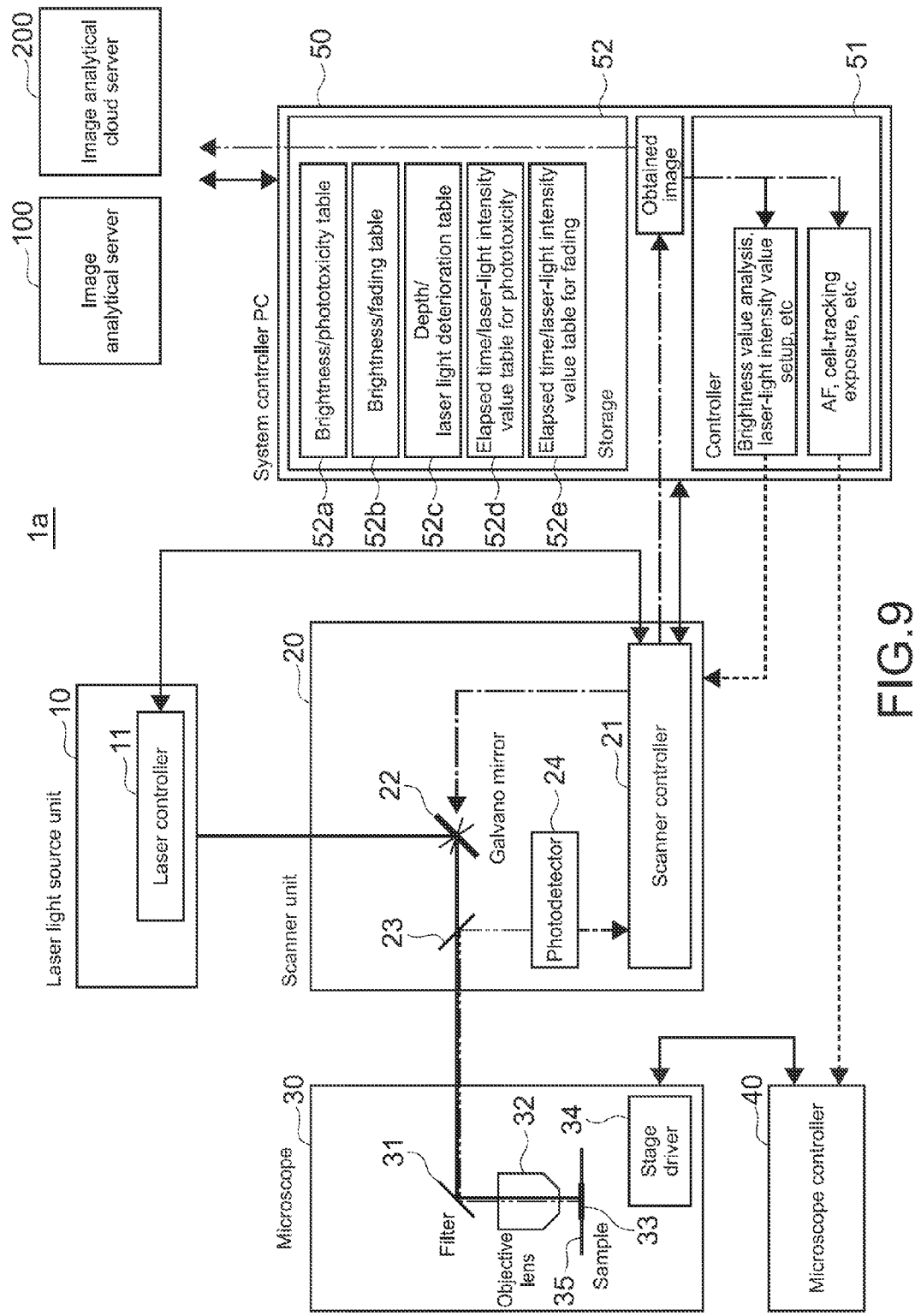

Firstly, the configuration of the microscope system 1a of the present technology will be described schematically. Note that the microscope system 1a is a laser scanning microscope system. FIG. 9 is a diagram schematically showing the configuration of the microscope system 1a.

The third embodiment is different from the first embodiment in that the storage 52 further stores elapsed time/laser-light intensity value tables for phototoxicity 52d (fourth relation information) and elapsed time/laser-light intensity value tables for fading 52e (fifth relation information).

[Five Kinds of Tables]

The storage 52 stores five kinds of tables, and the tables are used to control laser light. Here, the five kinds of tables will be described. The three kinds of tables out of the five kinds of tables are same as those of the first embodiment, i.e., the brightness/phototoxicity tables 52a, the brightness/fading tables 52b, and the depth/laser light deterioration tables 52c.

The additionally-stored elapsed time/laser-light intensity value table for phototoxicity 52d shows the relation between the elapsed time and the relative laser-light intensity value to reduce the phototoxicity. The line "control" of the graph of FIG. 7 shows this relation.

Moreover, the additionally-stored elapsed time/laser-light intensity value table for fading 52e shows the relation between the elapsed time and the relative laser-light intensity value to reduce fading. The relation is not shown in the drawings, but is similar to the line "control" of the graph of FIG. 7.

Those tables are previously created based on a plurality of measurements. In the previous measurement, the line "control" of the graph shows the control resultant values. However, in the main image-taking process, the line "control" of the graph shows control target values.

[Processing Flow]

The processing flow of this embodiment is the same as the processing flow of the first embodiment except for obtaining an elapsed time when a sample is observed and except for calculating a laser-light intensity value to be reset at the time of taking a fluorescence image. Because of this, here, the elapsed-time obtaining process and a method of calculating a laser-light intensity value will only be described.

(Elapsed-Time Obtaining Process)

Figure 10:
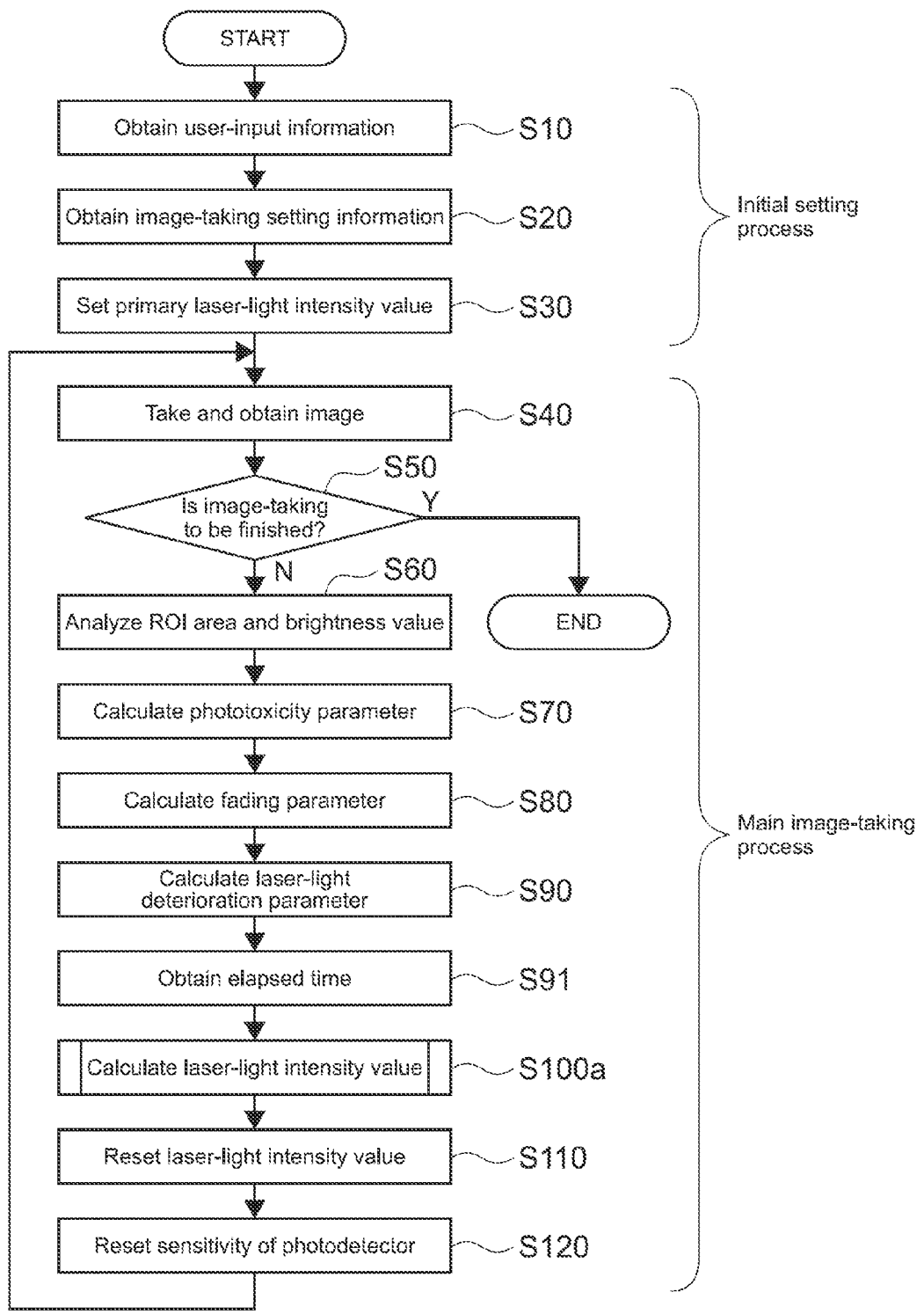
FIG. 10 is a flowchart illustrating the entire processing flow of the controller 51 of the system controller PC 50.

FIG. 10 is a flowchart illustrating the entire processing flow of the controller 51 of the system controller PC 50. The entire processing flow of the third embodiment is different from that of the first embodiment in that an elapsed time of observation is obtained (Step S91) after a laser-light deterioration parameter is obtained in Step S90, and in that the process of calculating a laser-light intensity value (Step S100a) is different from the process of Step S100.

(Method of Calculating Laser-Light Intensity Value)

Figure 11:
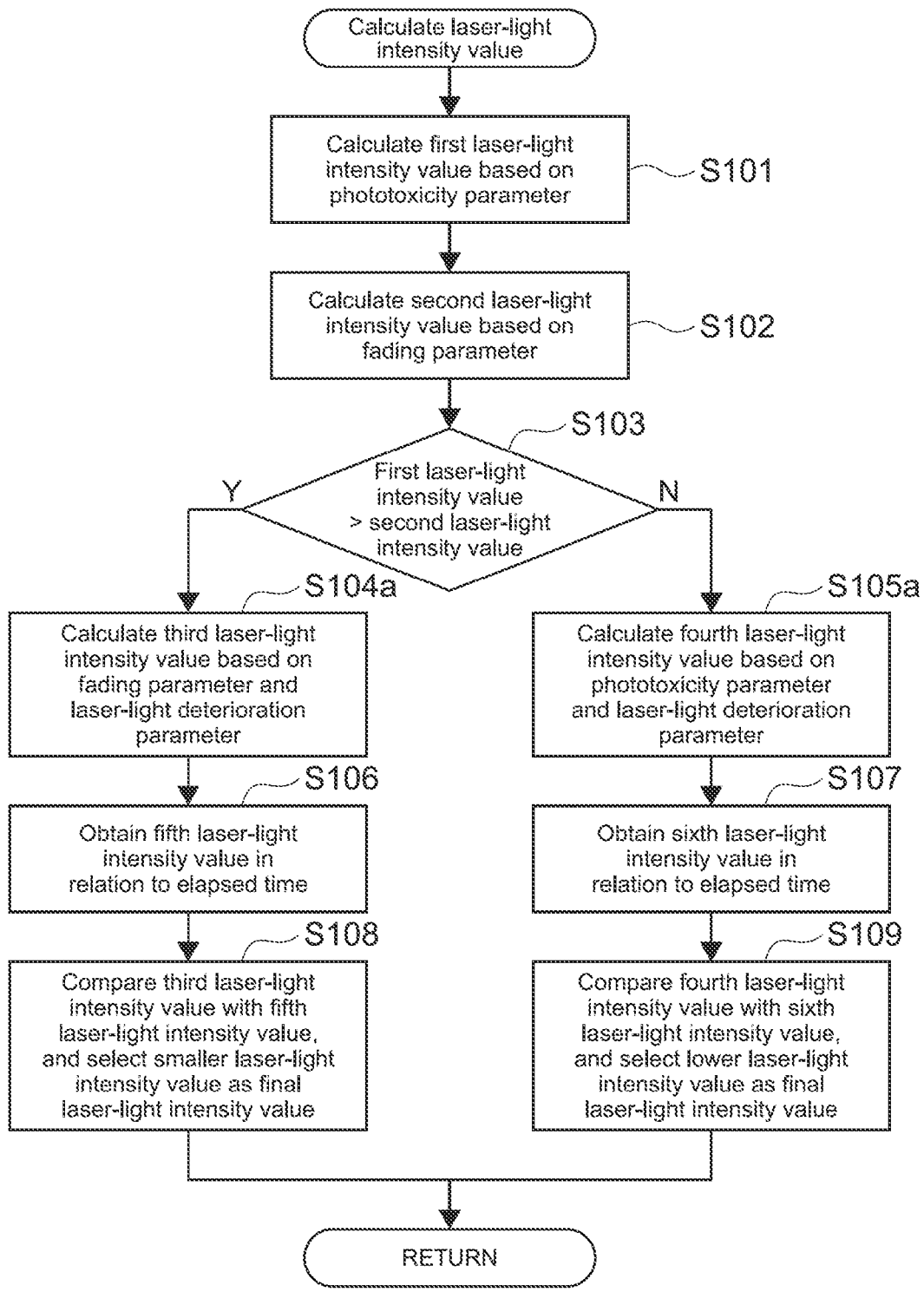
FIG. 11 is a flowchart illustrating the method of calculating a laser-light intensity value.

Here, as described above, a laser-light intensity value is calculated in Step S100a. A method of calculating a laser-light intensity value will be described. FIG. 11 is a flowchart illustrating the method of calculating a laser-light intensity value.

First, the controller 51 obtains a first laser-light intensity value based on the phototoxicity parameter calculated in Step S70 (Step S101).

Next, the controller 51 obtains a second laser-light intensity value based on the fading parameter calculated in Step S80 (Step S102).

Next, the controller 51 determines if the first laser-light intensity value is larger than the second laser-light intensity value (Step S103).

If the first laser-light intensity value is larger than the second laser-light intensity value (Step S103, Y), the controller 51 selects a fading parameter as a criterion for calculation. Then, the controller 51 calculates a third laser-light intensity value based on the selected fading parameter and the laser-light deterioration parameter (Step S104a).

Next, the controller 51 obtains a fifth laser-light intensity value in relation to the obtained elapsed time based on the elapsed time/laser-light intensity value table for fading 52e (Step S106).

Next, the controller 51 compares the calculated third laser-light intensity value with the calculated fifth laser-light intensity value. The controller 51 selects the smaller laser-light intensity value as a final laser-light intensity value to be reset (Step S108).

To the contrary, if the first laser-light intensity value is not larger than the second laser-light intensity value (Step S103, N), the controller 51 selects a phototoxicity parameter as a criterion for calculation. Then, the controller 51 calculates a fourth laser-light intensity value based on the selected phototoxicity parameter and the laser-light deterioration parameter (Step S105a).

Next, the controller 51 obtains a sixth laser-light intensity value in relation to the obtained elapsed time based on the elapsed time/laser-light intensity value table for phototoxicity 52d (Step S107).

Next, the controller 51 compares the calculated fourth laser-light intensity value with the calculated sixth laser-light intensity value. The controller 51 selects the lower laser-light intensity value as a final laser-light intensity value to be reset (Step S109).

The method of calculating a laser-light intensity value of Step S100a has been described.

Modification Example 1

In the third embodiment, both brightness values and elapsed time are fed back to reset a laser-light intensity value. To the contrary, in the modification example, a laser-light intensity value is reset only based on elapsed time.

In this case, only two kinds of tables, i.e., the elapsed time/laser-light intensity value tables for phototoxicity 52d and the elapsed time/laser-light intensity value tables for fading 52e, are used to obtain a laser-light intensity value.

Note that the configuration and the processing flow of this modification example correspond to part of the above-mentioned configuration and processing flow, and detailed description thereof will be omitted.

[Notes]

Moreover, the present technology is not limited to the above-mentioned embodiments, but may be variously modified within the gist of the present technology, as a matter of course.

[Other Configurations of the Present Technology]

Note that the present technology may employ the following configurations.

(1) A laser scanning microscope system, comprising:
  a laser light source capable of emitting laser light, the laser light being excitation light, a fluorescent-dyed biological sample being irradiated with the excitation light and emitting light;
  a photodetector configured
    to detect fluorescence emitted by the biological sample, and
    to output a signal corresponding to a brightness value; and
  a controller apparatus including
    storage configured to prestore first relation information, the first relation information including
      the plurality of laser-light intensity values, and
      information on at least one possible correlation between a phototoxicity degree and the brightness value in relation to each of the laser-light intensity values, the phototoxicity to the biological sample resulting from the laser light, and
    a controller configured
      to generate a fluorescence image having the brightness value based on the signal output from the photodetector,
      to calculate a brightness value representative of a ROI area based on the generated fluorescence image, and
      to refer to the first relation information, and to determine a laser-light intensity value satisfying tolerance of the phototoxicity based on the calculated representative brightness value.

(2) The laser scanning microscope system according to (1), wherein
  the storage is configured to further prestore second relation information, the second relation information including
    the plurality of laser-light intensity values, and
    information on at least one possible correlation between a fading degree of the fluorescence and the brightness value in relation to each of the laser-light intensity values, the fading of the fluorescence of the biological sample resulting from the laser light, and
  the controller is configured to select, based on the calculated representative brightness value, one of a laser-light intensity value satisfying a tolerance of the phototoxicity determined with reference to the first relation information and a laser-light intensity value satisfying a tolerance of the fading determined with reference to the second relation information, the selected laser-light intensity value being smaller than the other laser-light intensity value.

(3) The laser scanning microscope system according to (1) or (2), wherein
  the storage is configured to prestore third relation information, the third relation information showing a relation between a depth and an attenuation degree of the excitation light, the depth being between a surface of the biological sample and a position irradiated with the excitation light, and
  the controller is configured
    to refer to the third relation information, and
    to correct the selected laser-light intensity value.

(4) The laser scanning microscope system according to any one of (1) to (3), wherein
  the controller is configured to select sensitivity of the photodetector based on the corrected laser-light intensity value.

(5) The laser scanning microscope system according to any one of (1) to (4), wherein
  the storage is configured to prestore fourth relation information, the fourth relation information showing relation between an elapsed time of observation of the biological sample and a laser-light intensity value satisfying a tolerance of phototoxicity, the phototoxicity to the biological sample resulting from the laser light, and
  the controller is configured to select one of the corrected laser-light intensity value and a laser-light intensity value determined based on the elapsed time of observation with reference to the fourth relation information, the selected laser-light intensity value being lower than the other laser-light intensity value.

(6) The laser scanning microscope system according to any one of (1) to (4), wherein
  the storage is configured to prestore fifth relation information, the fifth relation information showing relation between an elapsed time of observation of the biological sample and a laser-light intensity value satisfying a tolerance of fading, the fading being given to the biological sample by the laser light, and
  the controller is configured to select one of the corrected laser-light intensity value and a laser-light intensity value determined based on the elapsed time of observation with reference to the fifth relation information, the selected laser-light intensity value being lower than the other laser-light intensity value.

(7) A method of setting a laser-light intensity value, comprising:
  emitting laser light, the laser light being excitation light, a fluorescent-dyed biological sample being irradiated with the excitation light and emitting light;
  detecting fluorescence emitted by the biological sample, and outputting a signal corresponding to a brightness value;
  prestoring relation information, the relation information including the plurality of laser-light intensity values, and information on at least one possible correlation between a phototoxicity degree and the brightness value in relation to each of the laser-light intensity values, the phototoxicity to the biological sample resulting from the laser light;
  generating a fluorescence image having the brightness value based on the output signal;
  calculating a brightness value representative of a ROI area based on the generated fluorescence image; and
  referring to the relation information, and determining a laser-light intensity value satisfying tolerance of the phototoxicity based on the calculated representative brightness value.

It should be understood by those skilled in the art that various modifications, combinations, sub-combinations and alterations may occur depending on design requirements and other factors insofar as they are within the scope of the appended claims or the equivalents thereof.

What is claimed is:

1. A laser scanning microscope system, comprising:
  a laser light source capable of emitting laser light, the laser light being excitation light, a fluorescent-dyed biological sample being irradiated with the excitation light and emitting light;
  a photodetector configured
    to detect fluorescence emitted by the biological sample, and to output a signal corresponding to a brightness value; and a controller apparatus including
storage configured to prestore first relation information, the first relation information including
the plurality of laser-light intensity values, and
information on at least one possible correlation between a phototoxicity degree and the brightness value in relation to each of the laser-light intensity values, the phototoxicity to the biological sample resulting from the laser light, and
a controller configured
to generate a fluorescence image having the brightness value based on the signal output from the photodetector,
to calculate a brightness value representative of a ROI area based on the generated fluorescence image, and
to refer to the first relation information, and to determine a laser-light intensity value satisfying tolerance of the phototoxicity based on the calculated representative brightness value;
wherein the storage is configured to further prestore second relation information, the second relation information including
the plurality of laser-light intensity values, and
information on at least one possible correlation between a fading degree of the fluorescence and the brightness value in relation to each of the laser-light intensity values, the fading of the fluorescence of the biological sample resulting from the laser light, and
the controller is configured to select, based on the calculated representative brightness value, one of a laser-light intensity value satisfying a tolerance of the phototoxicity determined with reference to the first relation information and a laser-light intensity value satisfying a tolerance of the fading determined with reference to the second relation information, the selected laser-light intensity value being smaller than the other laser-light intensity value.

2. The laser scanning microscope system according to claim 1, wherein
the storage is configured to prestore third relation information, the third relation information showing a relation between a depth and an attenuation degree of the excitation light, the depth being between a surface of the biological sample and a position irradiated with the excitation light, and
the controller is configured
to refer to the third relation information, and
to correct the selected laser-light intensity value.

3. The laser scanning microscope system according to claim 2, wherein
the controller is configured to select sensitivity of the photodetector based on the corrected laser-light intensity value.

4. The laser scanning microscope system according to claim 3, wherein
the storage is configured to prestore fourth relation information, the fourth relation information showing relation between an elapsed time of observation of the biological sample and a laser-light intensity value satisfying a tolerance of phototoxicity, the phototoxicity to the biological sample resulting from the laser light, and
the controller is configured to select one of the corrected laser-light intensity value and a laser-light intensity value determined based on the elapsed time of observation with reference to the fourth relation information, the selected laser-light intensity value being lower than the other laser-light intensity value.

5. The laser scanning microscope system according to claim 3, wherein
the storage is configured to prestore fifth relation information, the fifth relation information showing relation between an elapsed time of observation of the biological sample and a laser-light intensity value satisfying a tolerance of fading, the fading being given to the biological sample by the laser light, and
the controller is configured to select one of the corrected laser-light intensity value and a laser-light intensity value determined based on the elapsed time of observation with reference to the fifth relation information, the selected laser-light intensity value being lower than the other laser-light intensity value.

6. A method of setting a laser-light intensity value, comprising:
emitting laser light, the laser light being excitation light, a fluorescent-dyed biological sample being irradiated with the excitation light and emitting light;
detecting fluorescence emitted by the biological sample, and outputting a signal corresponding to a brightness value;
prestoring first relation information, the first relation information including the plurality of laser-light intensity values, and information on at least one possible correlation between a phototoxicity degree and the brightness value in relation to each of the laser-light intensity values, the phototoxicity to the biological sample resulting from the laser light;
prestoring second relation information, the second relation information including the plurality of laser-light intensity values, and information on at least one possible correlation between a fading degree of the fluorescence and the brightness value in relation to each of the laser-light intensity values, the fading of the fluorescence of the biological sample resulting from the laser light
generating a fluorescence image having the brightness value based on the output signal;
calculating a brightness value representative of a ROI area based on the generated fluorescence image;
referring to the relation information, and determining a laser-light intensity value satisfying tolerance of the phototoxicity based on the calculated representative brightness value; and
selecting, based on the calculated representative brightness value, one of a laser-light intensity value satisfying a tolerance of the phototoxicity determined with reference to the first relation information and a laser-light intensity value satisfying a tolerance of the fading determined with reference to the second relation information, the selected laser-light intensity value being smaller than the other laser-light intensity value.

* * * * *